United States Patent
Li et al.

(10) Patent No.: US 12,078,598 B2
(45) Date of Patent: Sep. 3, 2024

(54) METHOD AND SYSTEM FOR DETECTING PESTICIDE RESIDUES IN TEA BASED ON SURFACE-ENHANCED RAMAN SCATTERING (SERS) SENSOR

(71) Applicant: JIANGSU UNIVERSITY, Zhenjiang (CN)

(72) Inventors: Huanhuan Li, Zhenjiang (CN); Quansheng Chen, Zhenjiang (CN); Xiaofeng Luo, Zhenjiang (CN); Zhe Tang, Zhenjiang (CN); Wenhui Geng, Zhenjiang (CN)

(73) Assignee: JIANGSU UNIVERSITY, Zhenjiang (CN)

( * ) Notice: Subject to any disclaimer, the term of this patent is extended or adjusted under 35 U.S.C. 154(b) by 0 days.

(21) Appl. No.: 18/424,438

(22) Filed: Jan. 26, 2024

(65) Prior Publication Data

US 2024/0167959 A1    May 23, 2024

Related U.S. Application Data

(63) Continuation of application No. PCT/CN2023/133711, filed on Nov. 23, 2023.

(30) Foreign Application Priority Data

Apr. 19, 2023    (CN) .......................... 202310419439.7

(51) Int. Cl.
*G01N 21/65*    (2006.01)
*B01L 3/00*    (2006.01)
*G16C 20/20*   (2019.01)

(52) U.S. Cl.
CPC ............ *G01N 21/658* (2013.01); *B01L 3/502* (2013.01); *G16C 20/20* (2019.02);
(Continued)

(58) Field of Classification Search
None
See application file for complete search history.

(56) References Cited

U.S. PATENT DOCUMENTS

2021/0364441 A1* 11/2021 Zhu .................... G16C 20/20

FOREIGN PATENT DOCUMENTS

| CN | 109358033 A | 2/2019 |
| CN | 109752363 A | 5/2019 |

(Continued)

OTHER PUBLICATIONS

English Translation of CN 110146484 A, 2019 (Year: 2019).*

*Primary Examiner* — Lore R Jarrett (57) ABSTRACT

A method and a system for detecting pesticide residues in tea based on a surface-enhanced Raman scattering (SERS) sensor are provided. An octahedral gold-silver hollow cage-based sensor is prepared, mixed with a pesticide standard solution and analyzed to obtain SERS spectral data. The SERS spectral data is processed, and a quantitative model is established based on the processed SERS spectral data. Based on the quantitative model, the detection of thiram and pymetrozine in tea samples can be completed. By means of an octahedral cuprous oxide template, gold-silver octahedral hollow cage (Au—AgOHCs) nanomaterials are prepared by reduction of gold and silver ions and removal of the template by acid dissolution, so as to prepare the SERS sensor, which can be applied to the rapid and quantitative detection of thiram and pymetrozine in tea samples.

8 Claims, 3 Drawing Sheets

(52) U.S. Cl.
CPC ..... *B01L 2200/028* (2013.01); *B01L 2200/16* (2013.01); *B01L 2300/0663* (2013.01); *G01N 2333/415* (2013.01)

(56) References Cited

FOREIGN PATENT DOCUMENTS

| | | |
|---|---|---|
| CN | 110441282 A | 11/2019 |
| CN | 113552113 A | 10/2021 |

* cited by examiner

METHOD AND SYSTEM FOR DETECTING PESTICIDE RESIDUES IN TEA BASED ON SURFACE-ENHANCED RAMAN SCATTERING (SERS) SENSOR

CROSS-REFERENCE TO RELATED APPLICATIONS

This application is a continuation of International Patent Application No. PCT/CN2023/133711, filed on Nov. 23, 2023, which claims the benefit of priority from Chinese Patent Application No. 202310419439.7, filed on Apr. 19, 2023. The content of the aforementioned application, including any intervening amendments made thereto, is incorporated herein by reference in its entirety.

TECHNICAL FIELD

This application relates to pesticide residue detection, and more particularly to a method and a system for detecting pesticide residues in tea based on a surface-enhanced Raman scattering (SERS) sensor.

BACKGROUND

Tea contains a variety of inorganic minerals and organic compounds, such as caffeine, tannins, tea polyphenols, proteins, carbohydrates and multiple vitamins, etc., and has numerous pharmacological activities, such as refreshing the mind, clearing away heat, promoting digestion and eliminating phlegm. However, surface and internal accumulation of pesticides (e.g., insecticides and fungicides) will occur during the tea production and cultivation process. Long-term consumption of the tea containing pesticides may cause chronic diseases of various organs and threaten the human health. Therefore, enhancing the detection and monitoring of pesticide residues in tea is vital to ensure the quality and safety of the tea industry and protect the consumers' health. Among the common pesticide residues in tea, thiram (tetramethylthiuram disulfide) and pymetrozine are highly toxic, where the former may cause breathing difficulties, convulsions and fetal malformations, and the latter has been identified as a potential carcinogen. Maximum residue limits of pesticides in tea have been published in many countries. It has been clearly stipulated in the European Union that the maximum residue limits of the thiram and pymetrozine in tea are 0.2 mg/kg and 0.1 mg/kg, respectively. Conventional detection technologies for the pesticide residues in tea mainly include gas chromatography (GC), high-performance liquid chromatography (HPLC), gas chromatography-mass spectrometry (GC-MS) and high-performance liquid chromatography-mass spectrometry (HPLC-MS). These methods have high detection sensitivity and accuracy, but also have the following disadvantages: (1) complex pretreatment and cumbersome detection process; (2) high cost, expensive instrumentation and time-consuming analysis process; and (3) requirement of professional operators. Therefore, there is an urgent need for a fast, simple, and accurate method for detecting the pesticide residues in tea.

SUMMARY

In order to solve the technical problems in the prior art, this application introduces a deep learning model, and prepares a high-performance and highly-sensitive SERS sensor with an octahedral gold-silver hollow cage substrate, so as to achieve the rapid on-site detection of thiram and pymetrozine in tea.

In order to achieve the above purpose, this application provides a method for detecting pesticide residues in tea based on a SERS sensor, comprising:

(S1) preparing silver on a surface of an octahedral cuprous oxide template by reduction, adding an acid to dissolve the octahedral cuprous oxide template to obtain an octahedral silver hollow cage, and preparing gold on a surface of the octahedral silver hollow cage by reduction to obtain an octahedral gold-silver hollow cage sensor;

(S2) mixing the octahedral gold-silver hollow cage sensor with a pesticide standard solution followed by analysis using a Raman spectrometer to obtain SERS spectral data; processing the SERS spectral data by a Baseline Removal method and a Savitzky-Golay smoothing algorithm of a Python third-party library to eliminate a background interference and a fluorescence noise; and based on processed SERS spectral data, building a one-dimensional convolutional neural network by using a Keras framework to construct a quantitative model; and (S3) mixing the octahedral gold-silver hollow cage sensor with a tea sample pretreated according to a national standard method (SN/T 1541-2005) followed by analysis using the Raman spectrometer to collect sample SERS spectral data, processing the sample SERS spectral data by the Baseline Removal method and the Savitzky-Golay smoothing algorithm, and inputting processed sample SERS spectral data into the quantitative model, so as to obtain a predicted result, and then calculating a spiked recovery rate by comparing the predicted result with a spiked concentration of the tea sample.

In some embodiments, the step (S1) comprises:

(S1.1) reacting copper chloride dihydrate as a copper source with sodium hydroxide in the presence of polyvinylpyrrolidone as a stabilizer to obtain a copper hydroxide precipitate; reducing the copper hydroxide precipitate into cuprous oxide with ascorbic acid; and subjecting the cuprous oxide to centrifugal washing with an ethanol aqueous solution three times, and drying to obtain the octahedral cuprous oxide template;

(S1.2) preparing a silver layer on the surface of the octahedral cuprous oxide template from silver nitrate under cross-linking and reducing functions of sodium citrate and sodium borohydride, so as to obtain a silver-cuprous oxide octahedron; and adding a 1 vol. % acetic acid solution to a solution of the silver-cuprous oxide octahedron followed by stirring for 2 h and centrifugal washing to obtain the octahedral silver hollow cage; and (S1.3) reacting tetrachloroauric acid ($HAuCl_4$) with sodium borohydride in the presence of sodium citrate as a stabilizer on the surface of the octahedral silver hollow cage followed by washing multiple times with an aqueous ethanol solution and concentration to obtain the octahedral gold-silver hollow cage sensor.

In some embodiments, in step (S1.1), 4.5 g of the polyvinylpyrrolidone is added as the stabilizer; a volume ratio of the copper chloride dihydrate to the sodium hydroxide to the polyvinylpyrrolidone is 10:1:1; and a reaction mixture is aged for 3 h, washed 3 times with the aqueous ethanol solution, and then freeze-dried for 4-7 h to obtain the octahedral cuprous oxide template; a concentration of the copper chloride dihydrate is 0.01 mol/L; a concentration of the sodium hydroxide is 2 mol/L; and a concentration of the polyvinylpyrrolidone is 0.5-0.7 mol/L.

In some embodiments, in step (S1.2), 4.29 mg of the octahedral cuprous oxide template is dissolved in an ethanol solution, a volume ratio of sodium citrate to sodium borohydride to silver nitrate is 1.2 mL: 1 mL: 1 mL, and a reduction reaction time is 1-1.5 h; 1.2 mL of the 1 vol. % acetic acid solution is added, and an addition of the 1 vol. % acetic acid solution lasts for 2-5 s; and the stirring is performed at room temperature and 600-800 rpm for 2 h to dissolve the octahedral cuprous oxide template; a concentration of the sodium citrate is 30 mmol/L; a concentration of the sodium borohydride is 100 mmol/L; and a concentration of the silver nitrate is 10 mmol/L.

In some embodiments, in step (S1.3), a volume ratio of the sodium citrate to the sodium borohydride to the $HAuCl_4$ is 1.2 mL: 100 μL: 0.35 mL; a reduction reaction is performed at 28-35° C. for 30 min; and the octahedral gold-silver hollow cage sensor is stored in 5-10 mL of ethanol at 4° C. for later use; a concentration of the sodium citrate is 30 mmol/L; a concentration of the sodium borohydride is 100 mmol/L; a concentration of the $HAuCl_4$ is 5 mmol/L; and the concentration is performed such that a reaction product is 10-20 times concentrated.

In some embodiments, in step (S2), the maximum number of iterations of the Baseline Removal method is 15-20, and a weight value of a sum-of-square error between a fitted baseline and an original spectrum is updated iteratively; and the Savitzky-Golay smoothing algorithm has a window size of 7-11 and a fit degree of 5-7. In some embodiments, in step (S2), a structure of the quantitative model is formed by 4-8 one-dimensional convolution layers, 2-4 maximum pooling layers, 1-4 flatten layers and 1 fully-connected layer; each of the 4-8 one-dimensional convolution layers have a parameter dimension of 16-64 and a convolution kernel of 3; a pooling kernel size of each of the 2-4 maximum pooling layers is 3-5; the 1-4 flatten layers are configured to flatten multi-dimensional data into one-dimensional data for transition; and the 1 fully-connected layer is configured to output one feature.

In some embodiments, in step (S3), a volume ratio of each of a thiram standard solution and a pymetrozine standard solution to a solution of the octahedral gold-silver hollow cage is 4 μL: 5 μL; a reaction time is 5-10 min, and a concentration of each of the thiram standard solution and the pymetrozine standard solution is 0.01-1000 μg/mL.

This application also provides a system for detecting pesticide residues in tea based on a SERS sensor, comprising a preparation module, a building module and a detection module;

wherein the preparation module is configured to perform steps of:

preparing silver on a surface of an octahedral cuprous oxide template by reduction, adding an acid to dissolve the octahedral cuprous oxide template to obtain an octahedral silver hollow cage, and preparing gold on a surface of the octahedral silver hollow cage by reduction to obtain an octahedral gold-silver hollow cage sensor;

the building module is configured to perform steps of:

mixing the octahedral gold-silver hollow cage sensor with a pesticide standard solution followed by analysis using a Raman spectrometer to obtain SERS spectral data; processing the SERS spectral data by a Baseline Removal method and a Savitzky-Golay smoothing algorithm of a Python third-party library to eliminate a background interference and a fluorescence noise; and based on processed SERS spectral data, building a one-dimensional convolutional neural network by using a Keras framework to construct a quantitative model; and the detection module is configured to perform steps of:

mixing the octahedral gold-silver hollow cage sensor with a tea sample pretreated according to a national standard method (SN/T 1541-2005) followed by analysis using the Raman spectrometer to collect sample SERS spectral data, processing the sample SERS spectral data by the Baseline Removal method and the Savitzky-Golay smoothing algorithm, and inputting processed sample SERS spectral data into the quantitative model, so as to obtain a predicted result, and calculating a spiked recovery rate by comparing the predicted result with a spiked concentration of the tea sample.

Compared to the prior art, the present disclosure has the following beneficial effects.

1. This application uses the octahedral cuprous oxide template to prepare Au—Ag octahedral hollow cage (Au—AgOHCs) nanomaterials by reduction of gold and silver ions and acid dissolution to remove the template, so as to prepare the SERS sensor with excellent performance, which is used for rapid and quantitative detection of the thiram and pymetrozine in tea.

2. Compared with conventional smooth solid metal nanomaterials, hollow Au—AgOHCs with rough surfaces and sharp tips have stronger local electromagnetic fields and local plasmon resonance effects in their hotspot regions, which can significantly enhance Raman signals of target analytes, such that the Au—AgOHCs can be used as a SERS sensor with excellent performance.

3. Due to a bimetallic structure, the Au—AgOHCs sensor of this application has more stable antioxidant properties and excellent sensitivity, and its surface hotspot area will facilitate the adsorption detection of target analytes, such that it can be used as an excellent SERS sensor for detecting the pesticide residues in tea samples.

4. Through a deep learning convolutional neural network (CNN) model, features of the spectral data can be deeply mined, and a relationship between the analyte concentration and SERS spectral intensity can be accurately analyzed, so as to predict level of unknown pesticide residues in tea more accurately.

BRIEF DESCRIPTION OF THE DRAWINGS

In order to explain the technical solutions of the present application more clearly, the drawings required in the description of embodiments will be briefly introduced below. Obviously, presented in the drawings are merely some embodiments of the present application. For those of ordinary skill in the art, other drawings can be obtained based on these drawings without exerting creative efforts.

DETAILED DESCRIPTION OF EMBODIMENTS

The technical solutions in the embodiments of the present application will be clearly and completely described below with reference to the accompanying drawings of the present application. Obviously, described herein are merely some embodiments of the present application, rather than all embodiments. Based on the embodiments in this application, all other embodiments obtained by those of ordinary skill in the art without making creative efforts shall fall within the scope of the disclosure defined by the appended claims.

In order to make the above objects, features and advantages of the present application more obvious and understandable, the present application will be described in further detail below in conjunction with the accompanying drawings and specific embodiments.

Embodiment 1

An octahedral gold-silver hollow cage-based sensor was prepared as follows.

Step (1) Preparation of Cuprous Oxide Octahedron $CuCl_2 \cdot 2H_2O$ was used as a copper source, and reacted with NaOH in the presence of polyvinylpyrrolidone (PVP) as a stabilizer to obtain a copper hydroxide precipitate, which was reduced into cuprous oxide by ascorbic acid (AA), where a volume ratio of $CuCl_2 \cdot 2H_2O$ to NaOH to PVP was 10:1:1. The cuprous oxide was centrifugally washed three times with an aqueous ethanol solution and dried to obtain a cuprous oxide powder.

The specific steps were described as follows. First, a flask containing 100 mL of 0.01 M $CuCl_2 \cdot 2H_2O$ was added with 4.5 g of PVP, and then dropwise added with a NaOH aqueous solution (10 mL, 2 M). The mixed solution was stirred at 650 rpm and 55° C. for 30 min, dropwise added with 10 mL of a 0.6 M AA solution, and aged for 3 h to prepare the cuprous oxide. The precipitate was separated by centrifugation and washed three times with the aqueous ethanol solution to remove residual inorganic ions and polymers. Finally, the cuprous oxide ($Cu_2O$) was dried in a vacuum oven at 60° C. for 4-7 h to obtain a red $Cu_2O$ powder. In step (1), a concentration of the $CuCl_2 \cdot 2H_2O$ solution was 0.01 mol/L, a concentration of the NaOH aqueous solution was 2 mol/L, and a concentration of the PVP solution was 0.5-0.7 mol/L.

Step (2) Preparation of Silver-Cuprous Oxide (Ag—$Cu_2O$) Octahedron

The cuprous oxide octahedron was used as a template, and added with sodium citrate ($C_6H_5Na_3O_7$), $NaBH_4$ and $AgNO_3$. Under the cross-linking and reducing actions of $C_6H_5Na_3O_7$ and $NaBH_4$, a silver layer was grown on a surface of the cuprous oxide to obtain the Ag—$Cu_2O$ octahedron.

The specific steps were described as follows. 4.29 mg of the $Cu_2O$ red powder was dispersed ultrasonically in 100 mL of a 20% ethanol aqueous solution for 15 min. Then, 1.2 mL of a 30 mM $C_6H_5Na_3O_7$ solution and 1 mL of a 100 mM $NaBH_4$ solution were dropwise added to the $Cu_2O$ solution in sequence and stirred for 5 min. The reaction mixture was dropwise added with 1 mL of a 10 mM $AgNO_3$ solution and stirred at 600 rpm for 1 h. The color was observed to change from orange-yellow to reddish-yellow and then to dark cyan, which indicated that Ag—$Cu_2O$ was synthesized. In step (2), a volume ratio of the $C_6H_5Na_3O_7$ to $NaBH_4$ to $AgNO_3$ was 1.2 mL: 1 mL: 1 mL, and a reduction time was 1-1.5 h. A concentration of the $C_6H_5Na_3O_7$ solution was 30 mmol/L. A concentration of the $NaBH_4$ solution was 100 mmol/L. A concentration of the $AgNO_3$ solution was 10 mmol/L.

Step (3) Preparation of Octahedral Silver Hollow Cages (AgOHCs)

A solution of the Ag—$Cu_2O$ octahedron was added with a 1 vol. % acetic acid solution under stirring to dissolve the cuprous oxide octahedron template. The mixed solution was stirred for another 2 h, washed, and centrifuged to obtain the AgOHCs.

Specifically, the Ag—$Cu_2O$ octahedron solution was injected with 1.2 mL of the 1 vol. % acetic acid solution under stirring at 800 rpm, then reacted for 2 h to dissolve the cuprous oxide template, and finally centrifuged and washed to collect the AgOHCs.

Step (4) Preparation of Octahedral Gold-Silver Hollow Cages (Au—AgOHCs)

Tetrachloroauric acid ($HAuCl_4$) was reduced by sodium borohydride in the presence of sodium citrate as a stabilizer to form a gold layer on a surface of the silver cage.

Figure 1:
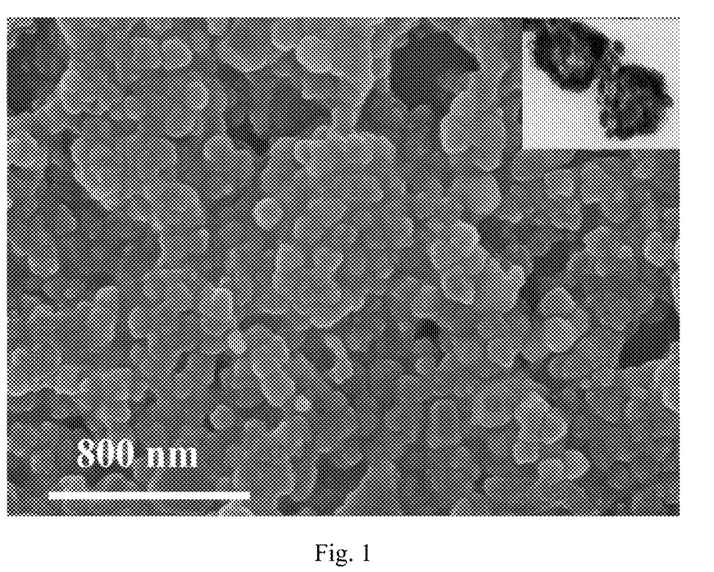
FIG. 1 is a scanning and transmission electron microscope image of an octahedral gold-silver hollow cage according to an embodiment of the present disclosure.

The specific steps were described as follows. The AgOHCs were dispersed in 100 mL of a 20% ethanol aqueous solution, to which 1.2 mL of a 30 mM $C_6H_5Na_3O_7$ aqueous solution and 100 μL of a 100 mM $NaBH_4$ solution were dropwise added. 2 min later, the mixed solution was dropwise added with 0.35 mL of a 5 mM $HAuCl_4$ aqueous solution, stirred for 30 min, and subjected to centrifugal washing three times with ethanol or pure water, and the precipitate was collected as the Au—AgOHCs and dispersed in 5 mL of ethanol for characterization and analysis (as shown in FIG. 1).

In order to remove the excess reducing agent, the reaction product was washed with ethanol and concentrated to obtain a purified Au—AgOHCs substrate. A concentration ratio of $C_6H_5Na_3O_7$ to $NaBH_4$ to $HAuCl_4$ was 20:6:1, and a volume ratio of $C_6H_5Na_3O_7$ to $NaBH_4$ to $HAuCl_4$ was 1.2 mL:100 μL:0.35 mL. A reduction temperature was 28-35° C., and a reduction time was 30 min. The Au—AgOHCs substrate was concentrated by 10 to 20 times by centrifugation, and stored in 5-10 mL of ethanol at 4° C. for later use.

A SERS sensor was used to detect thiram residues and pymetrozine residues in tea to obtain detection results.

Figure 2:
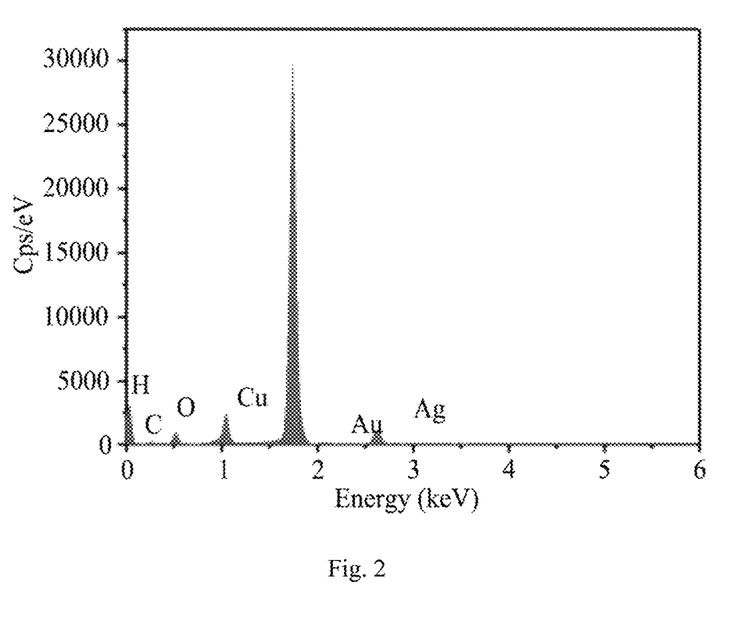
FIG. 2 shows an energy spectrum of an octahedral gold-silver hollow cage-based sensor according to an embodiment of the present disclosure.

4 μL of a 0.01-1000 μg/mL thiram standard solution and 4 μL of a 0.01-1000 μg/mL pymetrozine standard solution were mixed evenly with 5 μL of the Au—AgOHCs, respectively, and fully reacted for 5-10 min. Then, a portable Raman spectrometer was used to collect SERS spectra in a range of 200-2000 $cm^{-1}$ at room temperature. At the same time, a Baseline Removal method was used to remove random noise from an original spectrum, and a Savitzky-Golay smoothing algorithm was used to eliminate the background interference of SERS spectral data. The maximum number of iterations of the Baseline Removal method was 15-20, and a weight value of a sum-of-square error between a fitted baseline and the original spectrum was updated iteratively. The Savitzky-Golay smoothing algorithm had a window size of 7-11 and a fitting degree of 5-7. An energy spectrum of the octahedral gold-silver hollow cage was shown in FIG. 2.

Based on the processed SERS spectral data, a one-dimensional CNN was built based on a Keras framework to establish a quantitative model. In this embodiment, a structure of the CNN included 6 convolution layers for extracting data features, 3 maximum pooling layers for filtering maximum features, 1 flatten layer for flattening the multi-dimensional data into one-dimensional data for transition, and 1 fully-connected layer for feature output. The processed SERS spectral data was divided into a training set and a test set according to a ratio of 7:3, and data features were extracted to build the quantitative model. Determination coefficients of the CNN model for thiram and pymetrozine were up to 0.995 and 0.977, respectively, meeting the actual detection requirements. The convolution layers had a filter parameter of 16-64 and a convolution kernel of 3. A pooling kernel size of the pooling layers is 3-5. The flatten layers were configured to flatten multi-dimensional data into the one-dimensional data for transition. The fully-connected layer was configured to output 1 feature.

Finally, the quantitative model was used to complete the detection of the pesticide residues in tea samples.

The tea samples were crushed, sieved, extracted, and purified according to a national standard method (SN/T 1541-2005). 4 μL of a sample solution was mixed with 5 μL of the Au—AgOHCs to collect spectral data. The spectral data was substituted into the quantitative model to obtain prediction results.

Embodiment 2

Figure 3:
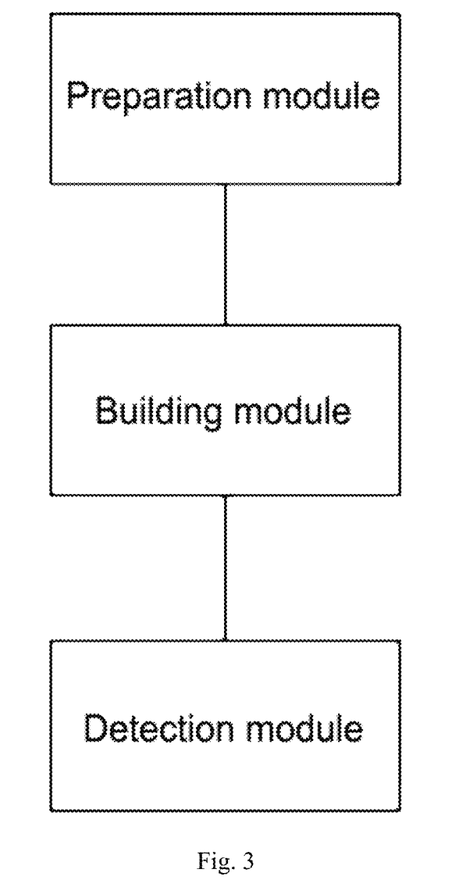
FIG. 3 is a structural diagram of a detection system according to an embodiment of the present disclosure.

A structural diagram of a detection system provided herein was presented in FIG. 3, including a preparation module, a building module and a detection module. The preparation module was configured to prepare Au—AgOHCs. The building module was configured to analyze a mixture of the Au—AgOHCs sensor and a pesticide standard solution to obtain SERS spectral data and build a quantitative model. The detection module was configured to detect thiram and pymetrozine in tea based on the quantitative model.

The Au—AgOHCs-based sensor was prepared by the preparation module through the following steps.

Step (1) Preparation of Cuprous Oxide Octahedron $CuCl_2 \cdot 2H_2O$ was used as a copper source, and reacted with NaOH in the presence of polyvinylpyrrolidone (PVP) as a stabilizer to obtain a copper hydroxide precipitate, which was reduced into cuprous oxide by ascorbic acid (AA), where a volume ratio of $CuCl_2 \cdot 2H_2O$ to NaOH to PVP was 10:1:1. The cuprous oxide was centrifugally washed three times with an aqueous ethanol solution and dried to obtain a cuprous oxide powder.

The specific steps were described as follows. First, a flask containing 100 mL of 0.01 M $CuCl_2 \cdot 2H_2O$ was added with 4.5 g of PVP, and then dropwise added with a NaOH aqueous solution (10 mL, 2 M). The mixed solution was stirred at 650 rpm and 55° C. for 30 min, dropwise added with 10 mL of a 0.6 MAA solution, and aged for 3 h to prepare the cuprous oxide. The precipitate was separated by centrifugation and washed three times with the aqueous ethanol solution to remove residual inorganic ions and polymers. Finally, the cuprous oxide ($Cu_2O$) was dried in a vacuum oven at 60° C. for 4-7 h to obtain a red $Cu_2O$ powder. In step (1), a concentration of the $CuCl_2 \cdot 2H_2O$ solution was 0.01 mol/L, a concentration of the NaOH aqueous solution was 2 mol/L, and a concentration of the PVP solution was 0.5-0.7 mol/L.

Step (2) Preparation of Silver-Cuprous Oxide (Ag—$Cu_2O$) Octahedron

The cuprous oxide octahedron was used as a template, and added with sodium citrate ($C_6H_5Na_3O_7$), $NaBH_4$ and $AgNO_3$. Under the cross-linking and reducing actions of $C_6H_5Na_3O_7$ and $NaBH_4$, a silver layer was grown on a surface of the cuprous oxide to obtain the Ag—$Cu_2O$ octahedron.

The specific steps were described as follows. 4.29 mg of the $Cu_2O$ red powder was dispersed ultrasonically in 100 mL of a 20% ethanol aqueous solution for 15 min. Then, 1.2 mL of a 30 mM $C_6H_5Na_3O_7$ solution and 1 mL of a 100 mM $NaBH_4$ solution were dropwise added to the $Cu_2O$ solution in sequence and stirred for 5 min. The reaction mixture was dropwise added with 1 mL of a 10 mM $AgNO_3$ solution and stirred at 600 rpm for 1 h. The color was observed to change from orange-yellow to reddish-yellow and then to dark cyan, which indicated that Ag—$Cu_2O$ was synthesized. In step (2), a volume ratio of the $C_6H_5Na_3O_7$ to $NaBH_4$ to $AgNO_3$ was 1.2 mL:1 mL: 1 mL, and a reduction time was 1-1.5 h. A concentration of the $C_6H_5Na_3O_7$ solution was 30 mmol/L. A concentration of the NaBH 4 solution was 100 mmol/L. A concentration of the $AgNO_3$ solution was 10 mmol/L.

Step (3) Preparation of Octahedral Silver Hollow Cages (AgOHCs)

A solution of the Ag—$Cu_2O$ octahedron was added with a 1 vol. % acetic acid solution under stirring to dissolve the cuprous oxide octahedron template. The mixed solution was stirred for another 2 h, washed, and centrifuged to obtain the AgOHCs.

Specifically, the Ag—$Cu_2O$ octahedron solution was injected with 1.2 mL of the 1 vol. % acetic acid solution under stirring at 800 rpm, then reacted for 2 h to dissolve the cuprous oxide template, and finally centrifuged and washed to collect the AgOHCs.

Step (4) Preparation of Octahedral Gold-Silver Hollow Cages (Au—AgOHCs)

Tetrachloroauric acid ($HAuCl_4$) was reduced by sodium borohydride in the presence of sodium citrate as a stabilizer to form a gold layer on a surface of the silver cage.

The specific steps were described as follows. The AgOHCs were dispersed in 100 mL of a 20% ethanol aqueous solution, to which 1.2 mL of a 30 mM $C_6H_5Na_3O_7$ aqueous solution and 100 μL of a 100 mM $NaBH_4$ solution were dropwise added. 2 min later, the mixed solution was dropwise added with 0.35 mL of a 5 mM $HAuCl_4$ aqueous solution, stirred for 30 min, and subjected to centrifugal washing three times with ethanol or pure water, and the precipitate was collected as the Au—AgOHCs and dispersed in 5 mL of ethanol for characterization and analysis (as shown in FIG. 1).

In order to remove the excess reducing agent, the reaction product was washed with ethanol and concentrated to obtain a purified Au—AgOHCs substrate. A concentration ratio of $C_6H_5Na_3O_7$ to $NaBH_4$ to $HAuCl_4$ was 20:6:1, and a volume ratio of $C_6H_5Na_3O_7$ to $NaBH_4$ to $HAuCl_4$ was 1.2 mL:100 μL:0.35 mL. A reduction temperature was 28-35° C., and a reduction time was 30 min. The Au—AgOHCs substrate was concentrated by 10 to 20 times by centrifugation, and stored in 5-10 mL of ethanol at 4° C. for later use.

A SERS sensor was used by the building module to detect thiram residues and pymetrozine residues in tea to obtain detection results.

4 μL of a 0.01-1000 μg/mL thiram standard solution and 4 μL of a 0.01-1000 μg/mL pymetrozine standard solution were mixed evenly with 5 μL of the Au—AgOHCs, respectively, and fully reacted for 5-10 min. Then, a portable Raman spectrometer was used to collect SERS spectra in a range of 200-2000 $cm^{-1}$ at room temperature. At the same time, a Baseline Removal method was used to remove random noise from an original spectrum, and a Savitzky-Golay smoothing algorithm was used to eliminate the background interference of SERS spectral data. The maximum number of iterations of the Baseline Removal method was 15-20, and a weight value of a sum-of-square error between a fitted baseline and the original spectrum was updated iteratively. The Savitzky-Golay smoothing algorithm had a window size of 7-11 and a fitting degree of 5-7. An energy spectrum of the octahedral gold-silver hollow cage was shown in FIG. 2.

Based on the processed SERS spectral data, a one-dimensional CNN was built based on a Keras framework to establish a quantitative model. In this embodiment, a structure of the CNN included 6 convolution layers for extracting data features, 3 maximum pooling layers for filtering maximum features, 1 flatten layer for flattening the multi-dimensional data into one-dimensional data for transition, and 1 fully-connected layer for feature output. The processed SERS spectral data was divided into a training set and a test set according to a ratio of 7:3, and data features were extracted to build the quantitative model. Determination coefficients of the CNN model for thiram and pymetrozine were up to 0.995 and 0.977, respectively, meeting the actual detection requirements. The convolution layers had a filter parameter of 16-64 and a convolution kernel of 3. A pooling kernel size of the pooling layers is 3-5. The flatten layers were configured to flatten multi-dimensional data into the one-dimensional data for transition. The fully-connected layer was configured to output 1 feature.

Finally, the quantitative model was used by the detection module to complete the detection of the pesticide residues in tea samples.

The tea samples were crushed, sieved, extracted, and purified according to a national standard method (SN/T 1541-2005). 4 µL of a sample solution was mixed with 5 µL of the Au—AgOHCs to collect spectral data. The spectral data was substituted into the quantitative model to obtain prediction results.

What is claimed is:

1. A method for detecting pesticide residues in tea based on a surface-enhanced Raman scattering (SERS) sensor, comprising:
    (S1) preparing silver on a surface of an octahedral cuprous oxide template by reduction, adding an acid to dissolve the octahedral cuprous oxide template to obtain an octahedral silver hollow cage, and preparing gold on a surface of the octahedral silver hollow cage by reduction to obtain an octahedral gold-silver hollow cage sensor;
    wherein the step (S1) comprises:
        (S1.1) reacting copper chloride dihydrate as a copper source with sodium hydroxide in the presence of polyvinylpyrrolidone as a stabilizer to obtain a copper hydroxide precipitate; reducing the copper hydroxide precipitate into cuprous oxide with ascorbic acid; and subjecting the cuprous oxide to centrifugal washing with an aqueous ethanol solution three times, and drying to obtain the octahedral cuprous oxide template;
        (S1.2) preparing a silver layer on the surface of the octahedral cuprous oxide template from silver nitrate in the presence of sodium citrate and sodium borohydride, so as to obtain a silver-cuprous oxide octahedron; and adding a 1 vol. % acetic acid solution to a solution of the silver-cuprous oxide octahedron followed by stirring for 2 h and centrifugal washing to obtain the octahedral silver hollow cage; and
        (S1.3) reacting tetrachloroauric acid ($HAuCl_4$) with sodium borohydride in the presence of sodium citrate as a stabilizer on the surface of the octahedral silver hollow cage followed by washing multiple times with the aqueous ethanol solution and concentration to obtain the octahedral gold-silver hollow cage sensor;
    (S2) mixing the octahedral gold-silver hollow cage sensor with a pesticide standard solution followed by analysis using a Raman spectrometer to obtain SERS spectral data; processing the SERS spectral data by a Baseline Removal method and a Savitzky-Golay smoothing algorithm of a Python third-party library to eliminate a background interference and a fluorescence noise; and based on processed SERS spectral data, building a one-dimensional convolutional neural network by using a Keras framework to construct a quantitative model; and
    (S3) mixing the octahedral gold-silver hollow cage sensor with a pretreated tea sample followed by analysis using the Raman spectrometer to collect sample SERS spectral data, processing the sample SERS spectral data by the Baseline Removal method and the Savitzky-Golay smoothing algorithm, and inputting processed sample SERS spectral data into the quantitative model, so as to obtain a predicted result; and then calculating a spiked recovery rate by comparing the predicted result with a spiked concentration of the tea sample.

2. The method of claim 1, wherein in step (S1.1), 4.5 g of the polyvinylpyrrolidone is added as the stabilizer; a volume ratio of the copper chloride dihydrate to the sodium hydroxide to the polyvinylpyrrolidone is 10:1:1; and a reaction mixture is aged for 3 h, washed 3 times with the aqueous ethanol solution, and then freeze-dried for 4-7 h to obtain the octahedral cuprous oxide template;
    a concentration of the copper chloride dihydrate is 0.01 mol/L;
    a concentration of the sodium hydroxide is 2 mol/L; and
    a concentration of the polyvinylpyrrolidone is 0.5-0.7 mol/L.

3. The method of claim 1, wherein in step (S1.2), 4.29 mg of the octahedral cuprous oxide template is dissolved in an ethanol solution, a volume ratio of sodium citrate to sodium borohydride to silver nitrate is 1.2 mL: 1 mL: 1 mL, and a reduction reaction time is 1-1.5 h; 1.2 mL of the 1 vol. % acetic acid solution is added, and an addition of the 1 vol. % acetic acid solution lasts for 2-5 s; and the stirring is performed at room temperature and 600-800 rpm for 2 h to dissolve the octahedral cuprous oxide template;
    a concentration of the sodium citrate is 30 mmol/L;
    a concentration of the sodium borohydride is 100 mmol/L; and
    a concentration of the silver nitrate is 10 mmol/L.

4. The method of claim 1, wherein in step (S1.3), a volume ratio of the sodium citrate to the sodium borohydride to the $HAuCl_4$ is 1.2 mL: 100 µL: 0.35 mL; a reduction reaction is performed at 28-35° C. for 30 min; and the octahedral gold-silver hollow cage sensor is stored in 5-10 mL of ethanol at 4° C. for later use;
    a concentration of the sodium citrate is 30 mmol/L;
    a concentration of the sodium borohydride is 100 mmol/L;
    a concentration of the $HAuCl_4$ is 5 mmol/L; and
    the concentration is performed such that a reaction product is 10-20 times concentrated.

5. The method of claim 1, wherein in step (S2), the maximum number of iterations range of the Baseline Removal method is 15-20, and a weight parameter value is the sum of squared errors between an iteratively updated fitted baseline and an original spectrum; and the Savitzky Golay smoothing algorithm has a window size parameter of 7-11 and a fitting order of 5-7.

6. The method of claim 1, wherein in step (S2), a structure of the quantitative model is formed by 4-8 one-dimensional convolution layers, 2-4 maximum pooling layers, 1-4 flatten layers and 1 fully-connected layer; each of the 4-8 one-dimensional convolution layers have a parameter dimension of 16-64 and a convolution kernel of 3; a pooling kernel size of each of the 2-4 maximum pooling layers is 3-5; the 1-4 flatten layers are configured to flatten multi-dimensional data into one-dimensional data for transition; and the 1 fully-connected layer is configured to output one feature.

7. The method of claim 1, wherein in step (S2), a volume ratio of each of a thiram standard solution and a pymetrozine standard solution to a solution of the octahedral gold-silver hollow cage is 4 µL:5 µL; a reaction time is 5-10 min, and a concentration of each of the thiram standard solution and the pymetrozine standard solution is 0.01-1000 µg/mL.

8. A system for detecting pesticide residues in tea based on a SERS sensor, comprising:
  a preparation module;
  a building module; and
  a detection module;
  wherein the preparation module is configured to perform steps of:
    (S1.1) reacting copper chloride dihydrate as a copper source with sodium hydroxide in the presence of polyvinylpyrrolidone as a stabilizer to obtain a copper hydroxide precipitate; reducing the copper hydroxide precipitate into cuprous oxide with ascorbic acid; and subjecting the cuprous oxide to centrifugal washing with an aqueous ethanol solution three times, and drying to obtain an octahedral cuprous oxide template;
    (S1.2) preparing a silver layer on the surface of the octahedral cuprous oxide template from silver nitrate in the presence of sodium citrate and sodium borohydride, so as to obtain a silver-cuprous oxide octahedron; and adding a 1 vol. % acetic acid solution to a solution of the silver-cuprous oxide octahedron followed by stirring for 2 h and centrifugal washing to obtain an octahedral silver hollow cage; and
    (S1.3) reacting tetrachloroauric acid ($HAuCl_4$) with sodium borohydride in the presence of sodium citrate as a stabilizer on a surface of the octahedral silver hollow cage followed by washing multiple times with an aqueous ethanol solution and concentration to obtain an octahedral gold-silver hollow cage sensor;
  the building module is configured to perform steps of:
  mixing the octahedral gold-silver hollow cage sensor with a pesticide standard solution followed by analysis using a Raman spectrometer to obtain SERS spectral data; processing the SERS spectral data by a Baseline Removal method and a Savitzky-Golay smoothing algorithm of a Python third-party library to eliminate a background interference and a fluorescence noise; and based on processed SERS spectral data, building a one-dimensional convolutional neural network by using a Keras framework to construct a quantitative model; and
  the detection module is configured to perform steps of:
  mixing the octahedral gold-silver hollow cage sensor with a pretreated tea sample followed by analysis using the Raman spectrometer to collect sample SERS spectral data, processing the sample SERS spectral data by the Baseline Removal method and the Savitzky-Golay smoothing algorithm, and inputting processed sample SERS spectral data into the quantitative model, so as to obtain a predicted result, and then calculating a spiked recovery rate by comparing the predicted result with a spiked concentration of the tea sample.

* * * * *